United States Patent [19]

Chalmers et al.

[11] Patent Number: 5,276,188

[45] Date of Patent: Jan. 4, 1994

[54] CRYSTALLIZATION PROCESS

[75] Inventors: Peter J. Chalmers, Sunbury; Andrew F. Kirby, Footscray; Roger P. Heath, Eltham, all of Australia

[73] Assignee: ICI Australia Operations Proprietary Limited, Melbourne, Australia

[21] Appl. No.: 798,247

[22] Filed: Nov. 26, 1991

[30] Foreign Application Priority Data

Nov. 27, 1990 [AU] Australia .................. PK3569

[51] Int. Cl.$^5$ .................. C07C 251/42; C07C 249/14; C07C 249/04
[52] U.S. Cl. .................................................. 564/256
[58] Field of Search .......................................... 564/256

[56] References Cited

U.S. PATENT DOCUMENTS

| Re. 32,489 | 9/1987 | Luo | 564/256 |
|---|---|---|---|
| 4,652,303 | 3/1987 | Watson et al. | 564/256 |
| 4,666,516 | 5/1987 | Watson et al. | 564/256 |
| 4,816,487 | 3/1989 | Schewe et al. | 564/256 |

*Primary Examiner*—Richard L. Raymond
*Assistant Examiner*—Peter G. O'Sullivan
*Attorney, Agent, or Firm*—Cushman, Darby & Cushman

[57] ABSTRACT

The invention relates to the compound 2-[1-(ethoxyimino) propyl]-3-hydroxy-5-(3-butyryl-2,4,6-trimethylphenyl)-cyclohex-2-en-1-one in the form of an anhydrous crystalline powder and a process for the preparation of said anhydrous crystalline powder.

1 Claim, No Drawings

CRYSTALLIZATION PROCESS

This invention relates to cyclohexanedione derivatives and to a method of manufacture.

Certain cyclohexanedione derivatives have been found to have outstanding herbicidal properties. As a result, an extensive patent literature has developed on this subject and typical examples include Australian patents 464555, 555884, 556148 and 566671.

Research by the applicants has resulted in a particularly promising herbicidal cyclohexanedione derivative having the chemical name 2-[1-(ethoxyimino)propyl]-3-hydroxy-5-(3-butyryl-2, 4,6-trimethylphenyl)cyclohex-2-en-1-one, which will hereinafter be referred to by its proposed common name "fenoxydim". This promise has, however, not yet been commercially realised because it has hitherto not proved possible to make fenoxydim in a physical form which is suitable for formulation as a commercial herbicide. The applicants have so far been able to isolate fenoxydim in two forms, the monohydrate form and the anhydrous form. The monohydrate form is a crystalline off-white solid which is easy to manipulate. It is, however, difficult to formulate, it melts at 30° C. (which makes storage in hot countries difficult) and it can dehydrate.

In view of these unfavourable physical properties of the monohydrate, it would be preferable to formulate herbicidal compositions from fenoxydim in its anhydrous form. However, anhydrous fenoxydim has so far only been obtained as a red-brown toffee-like or glass-like substance which is very inconvenient to store and use. Moreover, it is transportable as a solution of less than 90% purity and in some countries a substance of such purity is regarded as a formulated product rather than a raw material and attracts a higher import duty. Attempts to produce anhydrous fenoxydim in any form other than the toffee- or glass-like solid have hitherto failed.

It has now been found that it is possible to make a more easily useable form of fenoxydim. There is therefore provided, according to the present invention, anhydrous fenoxydim in the form of a crystalline powder.

The crystalline powder can easily be formulated into products. It has a melting-point of 82°-85° C. It is storage-stable, even in hot climates, and it is not hygroscopic. Being pure active ingredient, it occupies less space and can easily be transported. Most importantly, it makes available to the herbicides formulator the high activity of the substance.

The invention also provides a process for the preparation of anhydrous fenoxydim in the form of a crystalline powder comprising the steps of (a) preparing a solution of fenoxydim in a low-boiling hydrocarbon solvent;

(b) cooling the solution to at least 0° C.; and (c) filtering off the crystals thus formed.

The choice of low boiling (100° C. maximum) hydrocarbon solvent can be made from a wide range of such materials. There are, naturally, restrictions on the choice of material depending on circumstances and the skilled person will readily appreciate these restrictions. For example, one route to fenoxydim is via the corresponding trione by using a Friedel-Crafts reaction to provide the butyryl group. Such a process is described in Australian Patent Application No. 34225/84. If it is desired not to have a preparative stage followed by solution in fresh hydrocarbon solvent but to use the same hydrocarbon solvent throughout, the hydrocarbon solvent must obviously be one which is unaffected by Friedel-Craft reactions. Typical solvents for use in this invention are cyclohexane, alkanes, and petroleum spirits (boiling ranges 40°-60° C., 60°-40° C., 80°-1000° C.).

The anhydrous crystals are formed by cooling the solution of fenoxydim to at least 0° C., more preferably to at least −5° C. and most preferably to at least −10° C. This causes the fenoxydim to crystallise as anhydrous crystals which can then be recovered and dried.

There are a number of variations on the process which make it more efficient. For example, prior to cooling to at least −5° C., it is preferred to cool the solution to 0° C. with ice and then seed with a crystal of fenoxydim. This results in a greater yield.

The invention is further described with reference to the following examples.

EXAMPLE 1

A crude 2-[1-(ethyoxyimino)propyl]-3-hydroxy-5-(3-butyryl-2, 4,6-trimethylphenyl)cyclohex-2-en-1-one used in the crystallization process of the invention may be prepared, for example, by reaction of 3-hydroxy-5-(2,4,6-trimethylphenyl)-2-propionyl-cyclohex-2-en-1-one with n-butyryl chloride in accordance with the process of Example 1 of Australian Patent Application No. 34225/84 and treating the 3-hydroxy-5-(3-butyryl-2,4,6-trimethylphenyl )-2-propionylcyclohex-2-en-1-one so obtained with ethoxyamine.

A crude cyclohexane solution of 2-[1-(ethoxyimino)-propyl]-3-hydroxy-5-(3-butyryl-2, 4,6-trimethylphenyl) cyclohex-2-en-1-one was washed with a solution bicarbonate solution, separated and evaporated with azeotropic removal of water. The residual brown gel was dissolved in petroleum spirit bp 80°-100° C. (120 ml) and evaporated to dryness again to remove traces of cyclohexane. The residue was dissolved in hot petroleum spirit bp 80°-100° C. (150 ml) and cooled to less than 10° C. The solution was seeded with a crystal of anhydrous fenoxydim and further cooled to 0° C. until crystallization was observed. The mixture was then cooled to −10° C. and stirred rapidly. The precipitate was filtered off, washed twice with petroleum spirit and air dried to give fenoxydim (71.2 g, 89%) as a fine white anhydrous solid.

NMR analysis of the brown gel and the final white powder showed the compounds to be the same but infra-red analysis of the solid compounds showed substantial differences. The brown gel showed significant peaks at 3206, 2968, 2934, 2876, 2578, 1701, 1595 and 1392 cm$^{-1}$, whereas the anhydrous solid showed peaks at 3386, 2970, 2937, 2878, 1702, 1642, 1606, 1553, 1395 and 1045 cm$^{-1}$. This indicates the presence of a different isomeric form of fenoxydim.

We claim:

1. The compound 2-[1-(ethoxyimino)propyl]-3-6 hydroxy-5-(3-butyryl-21,4,6-trimethylphenyl)-cyclohex-2en-1-one in the form of an anhydrous crystalline powder.

* * * * *